(12) United States Patent
Ohman et al.

(10) Patent No.: US 8,025,854 B2
(45) Date of Patent: Sep. 27, 2011

(54) MICRO FLUIDIC STRUCTURES

(75) Inventors: Ove Ohman, Uppsala (SE); Ib Mendel-Hartvig, Uppsala (SE)

(73) Assignee: AMIC AB (SE)

( * ) Notice: Subject to any disclaimer, the term of this patent is extended or adjusted under 35 U.S.C. 154(b) by 1195 days.

(21) Appl. No.: 10/492,453

(22) PCT Filed: Jun. 4, 2003

(86) PCT No.: PCT/SE03/00919
§ 371 (c)(1),
(2), (4) Date: Oct. 18, 2004

(87) PCT Pub. No.: WO03/103835
PCT Pub. Date: Dec. 18, 2003

(65) Prior Publication Data
US 2005/0042766 A1    Feb. 24, 2005

(30) Foreign Application Priority Data
Jun. 7, 2002    (SE) .................................... 0201738

(51) Int. Cl.
*B01L 3/00* (2006.01)
(52) U.S. Cl. ................ 422/507; 422/554; 422/551
(58) Field of Classification Search ........... 422/102, 422/104, 507, 554, 551
See application file for complete search history.

(56) References Cited

U.S. PATENT DOCUMENTS

| | | | |
|---|---|---|---|
| 5,124,172 A * | 6/1992 | Burrell et al. ................ 435/4 |
| 5,540,888 A | 7/1996 | Bunce et al. | |
| 5,837,115 A | 11/1998 | Austin et al. | |
| 6,143,576 A | 11/2000 | Buechler | |
| 6,156,270 A | 12/2000 | Buechler | |
| 6,156,273 A | 12/2000 | Regnier et al. | |
| 6,296,020 B1 | 10/2001 | McNeely et al. | |
| 6,454,924 B2 * | 9/2002 | Jedrzejewski et al. ........ 204/601 |
| 6,767,510 B1 | 7/2004 | Buechler | |
| 2002/0039783 A1 * | 4/2002 | McMillan et al. ......... 435/287.2 |
| 2003/0035758 A1 | 2/2003 | Buechler et al. | |
| 2004/0077103 A1 | 4/2004 | Buechler | |
| 2004/0126767 A1 | 7/2004 | Anderberg et al. | |
| 2005/0136552 A1 | 6/2005 | Buechler | |

FOREIGN PATENT DOCUMENTS

EP    1120164    8/2001
JP    2002-001102 A    1/2002

OTHER PUBLICATIONS

International Search Report mailed Aug. 8, 2003, for PCT patent application No. PCT/SE03/00919 filed on Jun. 4, 2003, 2 pages.

* cited by examiner

*Primary Examiner* — Natalia Levkovich
(74) *Attorney, Agent, or Firm* — Hiscock & Barclay, LLP

(57) ABSTRACT

The invention relates to a micro fluidic system comprising a substrate, and, provided on said substrate, at least one flow path interconnecting with functional means in which liquid samples can be treated by desired procedures. The flow paths are laid out to form a pattern for the transport of liquid samples to and from said functional means. These flow paths comprise a plurality of micro posts protruding upwards from said substrate, the spacing between the micro posts being small enough to induce a capillary action in a liquid sample applied anywhere within any of said flow paths, so as to force said liquid to move from where said liquid sample was applied.

24 Claims, 9 Drawing Sheets

MICRO FLUIDIC STRUCTURES

FIELD OF THE INVENTION

The present invention relates to micro fluidic structures, and in particular to a micro structure defining a liquid flow system, wherein capillary action is utilized as the main driving force for liquid transport through said structure.

The micro fluidic structure according to the invention is useful in various fields of application such as miniaturized bioassays, preparatory steps for such assays, separation, electrophoresis, capillary chromatography, micro reaction cavity procedures, miniaturized liquid communication units, biosensor flow cells and the like.

BACKGROUND OF THE INVENTION

Liquid transport through channels or structures on a micro scale has important implications in a number of different technologies.

Controlled transport of fluids through micro channels has been a challenge, with the microstructure itself imparting difficulties not found on a larger scale. The driving force utilized in most micro channel structures depends on electroendosmosis, gravitational forces, external pressure or capillary migration.

Surface materials often have unbound electrons, polar moieties, or other features generating a surface charge or reactivity. Surface characteristics often have a more pronounced impact on a micro scale system than on a larger structure. This is particularly true in micro systems where the fluid flow is driven by attractions between liquids and the surface materials through which they are transported.

In a closed capillary the driving force is usually represented by the equation:

$$h = 2\sigma_{gl}\cos(\theta_c)/g\rho \tag{1}$$

where h=the height of a fluid within a capillary tube; $\theta_c$=the contact angle of the fluid with the capillary tube material.

If the contact angle of the capillary tube material, with respect to the fluid, is less than 90°, the material is considered hydrophilic. If the contact angle of the tube material, with respect to the fluid, is greater than 90°, the material is considered hydrophobic. $\sigma_{gl}$ represents the surface tension of the fluid with respect to the air (millijoules/m$^2$), g is the gravitational constant (m/s$^2$), r is the radius of the capillary tube (m), and $\rho$ is the fluid density (kg/n$^3$).

Planar micro structures have been developed in which a number of grooves or channels are made, typically such a planar structure is produced by etching grooves in a semiconductor substrate, such as a silicon wafer, and then covering the etched surface by a cover plate to complete the channels. Such structures are, however, rather time consuming and expensive to produce.

Further, when such structures need to be customized, e.g. by the addition of chemical reagents, the functionalization of surfaces etc., these steps often need to be performed by somebody other than the producer of the micro structure. In practice, the micro structures are manufactured at one location and shipped to another facility e.g. for the addition of reagents, whereupon they often need to be returned to the manufacturer for closing and sealing. One aim of the present invention is therefore to make available a micro structure offering greater flexibility and ease, in particular with regard to the post-production customization.

Systems used at present utilize external means, e.g. gravity, centrifugal force (spinning of disk elements with micro channels on the surface), or pressure to impose transport of liquids in channels. Also electric fields can be used to impose transport of dissolved charged species in micro systems. To this end, external auxiliary equipment is employed, such as a motor to generate the spinning of a disk, pumps to create pressure, electrodes and power supplies to apply electric fields etc. Such equipment is costly and sometimes rather complex. Furthermore, in certain cases the forces involved in the above mentioned methods could have detrimental effects on sensitive substances. Another aim of the invention is therefore to make available a micro structure with built-in functionality, removing or reducing the need of external means to impose liquid transport.

PRIOR ART

EP 1 120 164 describes the use of a plurality of micro structures in a capillary pathway, said pathway having at least one curved portion, the pathway comprising a base, an inner wall defined by a first radius from a center point and defined by a second radius greater than the first radius, the inner wall and outer wall being fixed to the base and defining the lateral boundaries of the capillary pathway, and a lid extending at least from the inner wall to the outer wall covering the capillary pathway. It becomes clear that the micro structures themselves do not form a capillary pathway, but only influence the flow as the fluid travels around curved portions in said capillary pathway, the flow being somewhat slower near the inner wall of a curved portion than near the outer wall.

U.S. Pat. No. 5,885,527, cited in the above EP 1 120 164 describes assay devices including micro structures forming reaction barriers. These reaction barriers are formed by corrugated or otherwise patterned surfaces, having grooves which together with a cover or top member form narrow channels between different chambers in said device. It is clear from the description and figures, that the capillary channels are indeed formed only when a top member is placed on a bottom member a capillary distance apart. Further, the top and bottom members may be married, the various chambers sealed and the capillaries formed by a number of techniques, including but not limited to, gluing, welding by ultrasound, riveting and the like.

U.S. Pat. No. 5,837,115 discloses a sorting apparatus and method for fractionating and simultaneously viewing individual micro structures, such as cells, viruses, macro molecules or minute particles in a fluid medium. The aim of the invention is to replace agarose gels and other traditionally used fractionation media with a lattice structure with uniform distribution, size and shape of the hindered environment. The hindered environment may be formed by posts, bunkers, v-shaped or cup-shaped structures, forming sifting means for the cells, viruses etc under study. This structure is covered by ceiling means positioned over the lattice causing the migration of microstructures in essentially a single layer through the sifting means exclusively. The invention according to U.S. Pat. No. 5,837,115 does not seem to consider capillary forces, but instead suggests the provision of electrodes for generating an electric field over the lattice structure.

It is widely known to use channels filled with porous material, as exemplified in U.S. Pat. No. 5,540,888, said porous material having sub-channels divided by slots, liquid impermeable separating portions etc., and containing reagent regions and sample application regions. Filter paper is often the material of choice, and there exists a wide range of technologies for applying reagents to this material.

It remains to make available micro fluidic structures integrated in a support which is suitable for mass production, and in a configuration which makes the micro fluidic device, comprising said structures, easily handled in the down-stream production process, and in particular in the customization of the device.

In view of the drawbacks of having to use relatively complex external equipment for influencing liquid flow, which in addition could damage the samples, it would be both desirable and advantageous to enable "automatic" transport of sensitive substances without use of complex devices and without subjecting the substances to the risk of being altered, e.g. denatured or otherwise damaged.

One aim of the present invention is therefore to provide a micro-fluidic structure, i.e. a geometric micro structure defining a liquid flow system, suitable for capillary transport of liquids and which is inexpensive to produce, optionally permitting a disposable type product, optionally having branched flow channels, optionally exhibiting local surface characteristics, and providing great freedom in choice of material, e.g. with regard to surface, optical and electric properties.

Further aims underlying the invention, as well as the advantages associated with the inventive solution and its embodiments, will become apparent from the following description and examples, together with the attached claims and drawings.

SUMMARY OF THE INVENTION

The above aims are achieved with the present invention by employing the phenomenon of capillary action to drive liquid flow through open micro structures provided on solid substrates. In its widest scope, the micro fluidic structure according to the present invention comprises various forms of geometric micro structures defining the desired liquid flow system.

The present invention in its broadest aspect provides a flow path consisting of a multitude of micro structures inducing and/or facilitating the flow of fluids through said flow path, as well as methods where this flow path is used.

The invention in particular provides a micro fluidic system comprising a substrate, and, provided on said substrate, at least one flow path and functional means in which liquid samples can be treated by desired procedures, wherein said at least one flow path is/are laid out to form a pattern for the transport of liquid samples to, through and from said functional means; wherein the flow path consists of a plurality of micro posts protruding upwards from said substrate; wherein the spacing between the micro posts is such as to induce a capillary action in a liquid sample applied anywhere to said flow path, so as to force said liquid to move from where said liquid sample was applied.

The functional means may comprise one or more of chemical reactors, separation means, heating means, means for irradiation with electromagnetic radiation, magnetic means for trapping magnetic components of said liquid within said functional means, electrodes for applying voltage to the liquid over a selected region, or any other device or means for chemically, biologically or physically treating liquid samples located within said functional means.

BRIEF DESCRIPTION OF THE DRAWINGS

The present invention will be described in closer detail in the following description and non-limiting examples, with reference to the attached claims and drawings, in which:

DESCRIPTION OF PREFERRED EMBODIMENTS OF THE INVENTION

Figure 1:
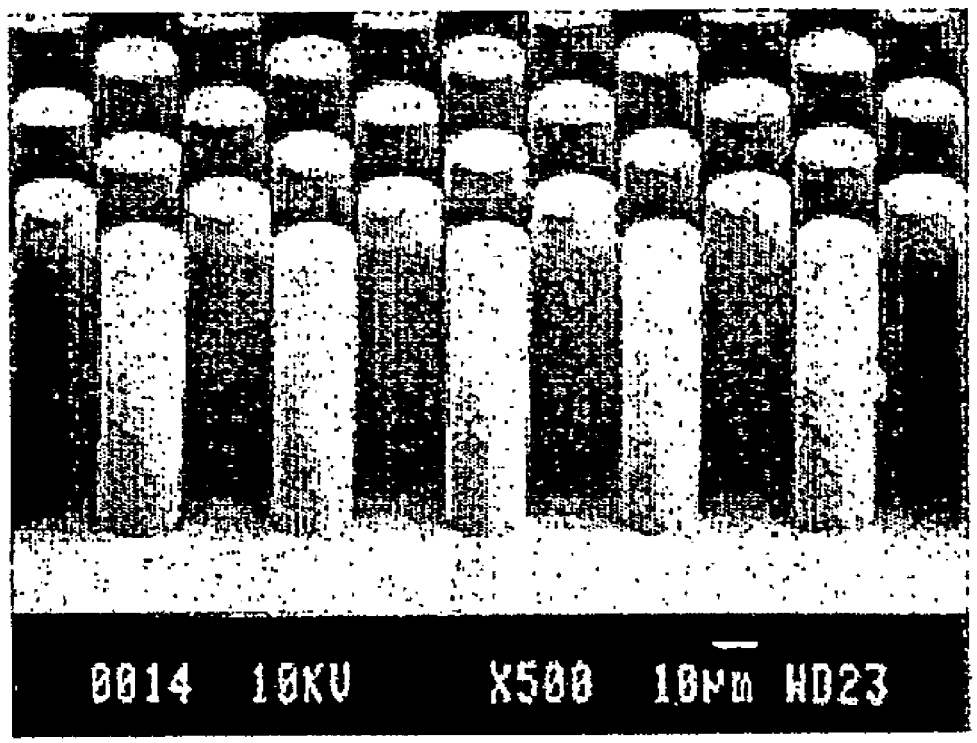
FIG. 1 is a SEM microphotograph of a portion of a structure according to the invention.
Figure 2:
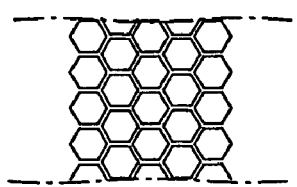
FIGS. 2 through 6 show cross sections of the capillary structure according different embodiments of the present invention.
Figure 3:
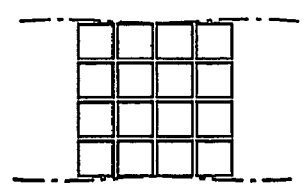
Figure 4:
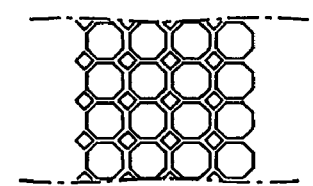
Figure 5:
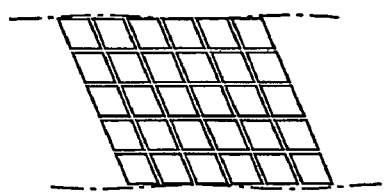
Figure 6:
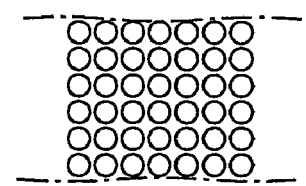

Before the present invention is described, it is to be understood that the terminology employed herein is used for the purpose of describing particular embodiments only and is not intended to be limiting, since the scope of the present invention will be limited only by the appended claims and equivalents thereof.

The following terms will be used:

The prefix "micro" as in micro fluidic, micro structure etc is used to define a device or a process which comprises or involves at least one feature having a length, width or height normally expressed in micrometers (μm, $1 \times 10^{-6}$ m).

The prefix "nano" is here used in its generally accepted meaning, as in nanometer (nm, $1 \times 10^{-9}$ m).

The expression "passive" as used in e.g. "passive control" or "passive fluid dynamics" refers for the purposes of this invention to a control that is not influenced by actions taken during a process that is to be carried out, but rather the control is determined by fixed system parameters, which are design dependent. The passive control is generated by using the natural capillary forces that exist on a micro scale.

The term "open" in this context means that the flow paths defined by the micro structures are accessible from above, and have no cover or lid which takes part in creating the capillary flow. The above definition does however not rule out that a secondary cover or lid, at a distance from the micro structure, can be provided.

The term "hydrophilic groups" refers to substrates and substances having polar and/or charged groups, such as hydroxyl, carboxyl, amino, sulphonate, thiol, aldehyde etc.

The term "hydrophobic structure" refers to substrates and substances having non polar structures.

The term "chemically reactive groups" refers to all organic and inorganic groups used in covalent coupling of molecules to solid faces and known to persons skilled in the art, such a hydroxyl, carboxyl, amino, sulphonate, thiol, aldehyde etc.

The term "biological affinity" refers to substances having specific binding of a substance or a defined group of related substances. Exemplary substances are antibodies, antigens, haptens, biotin, avidin, lectin, sugar, nucleic acids, hormones and their receptors.

The invention in its broadest aspect provides a multi-element capillary structure adapted to facilitate and/or effect the capillary flow of liquids along said structure in open systems by using micro-structures provided on or in said structure. Advantage is taken of the surface effects between a fluid and the surfaces contacting the fluid. These surface effects come into play at the micro scale.

In particular there is provided devices having a structure comprising at least one liquid flow path, optionally connecting different processing compartments within said structure for carrying out a number of different unit operations. Examples of such processing compartments, elements and/or devices are chemical reaction compartments, incubation compartments, wash compartments or elements, flow control elements, measurement elements, time gates, separation means, heating means, means for irradiation with electromagnetic radiation, magnetic means for trapping magnetic components of said liquid within said functional means, electrodes for applying voltage to the liquid over a selected region, detectors for detecting physical or chemical properties e.g, temperature, pH, viscosity, absorbance etc., or any other device or means for chemically, biologically or physically treating a liquid sample or reaction mixture located within or passing through said compartment, element and/or device.

In order to clarify the principle behind the inventive concept the following illustration is given:

Consider a simple example of the effect of surface forces, such as demonstrated when water is drawn into an glass capillary without any outside pressure being applied. This is caused by the surface tension between the water and the glass surface, which pulls water into the capillary. The narrower the capillary, the greater the effect of the force that pulls the water into the capillary. This is often referred to as the capillary force.

One physical parameter that characterizes the magnitude of the capillary force is the contact angle between the water and the surrounding material. For contact angles less than 90°, the material, e.g., glass, is considered to be hydrophilic and water is drawn up into the capillary space. When the material has a contact angle greater than 90° it is considered hydrophobic. In the hydrophobic case, pressure is required to force water into the space. The narrower the capillary, the greater the force that is required. However, in both cases once water has been introduced into the capillary, the flow rates of the water depend more on pressure gradients and friction and less on whether the material is hydrophobic or hydrophilic.

In order to achieve the desired function of the micro structures forming the flow paths of the present invention, the contact area between liquid and the surface of the solid material is maximized, whereby the capillary force increases so that a fluid flow within or along the flow path according to the invention is spontaneously induced and maintained over a desired period of time.

This process represents what can be referred to as "passive fluid dynamics". The present inventors have found that it is advantageous to use such passive fluid dynamics to control and drive the flow of fluid in open micro channels or structures on a surface. For example, the passive nature of the transport mechanism according to the invention makes it direction independent, as compared to a system on a spinning disk where mainly a radial transport is possible. Transport by application of an electric field is mainly bi-directional at best. Capillary flow can be induced in any direction, provided the pattern of micro structures forming the flow paths is designed properly. A person skilled in the field of designing micro structures and fluid flow cannerls on such structures will be able to apply the teaching of the invention without undue experimentation.

FIG. 1 shows a SEM microphotograph of an example of a micro fluidic structure embodying the inventive concept. It is evident from the picture that the micro posts have an identical shaped, a regular form and are evenly spaced over the support structure. Also the surface between the micro posts is even. A skilled person will recognize that the micro posts shown in the SEM microphotograph have a high aspect ratio. In this example, the micro posts were about 100 µm high, had a diameter of 20 µm and a center-to-center distance of 30 µm. This accounts for an aspect ratio of 1:5. It is generally held that an aspect ration >1:2 is a high aspect ratio.

FIGS. 2 through 6 show a number of different cross sections of the micro structures forming the fluid flow path according to the present invention. The micro structures or micro posts can have a cross section which is one of circular, elliptical, rhombic, triangular, square, rectangular, heptagonal, hexagonal etc or a combination thereof. The cross section can also be any fraction of the above forms, such as a half-circle, a crescent, U-shaped, X-shaped etc as long as the dimension and center-to-center distance of the individual microstructures is such, that capillary flow is induced without the provision of any lid or cover, limiting the flow path.

Figure 7:
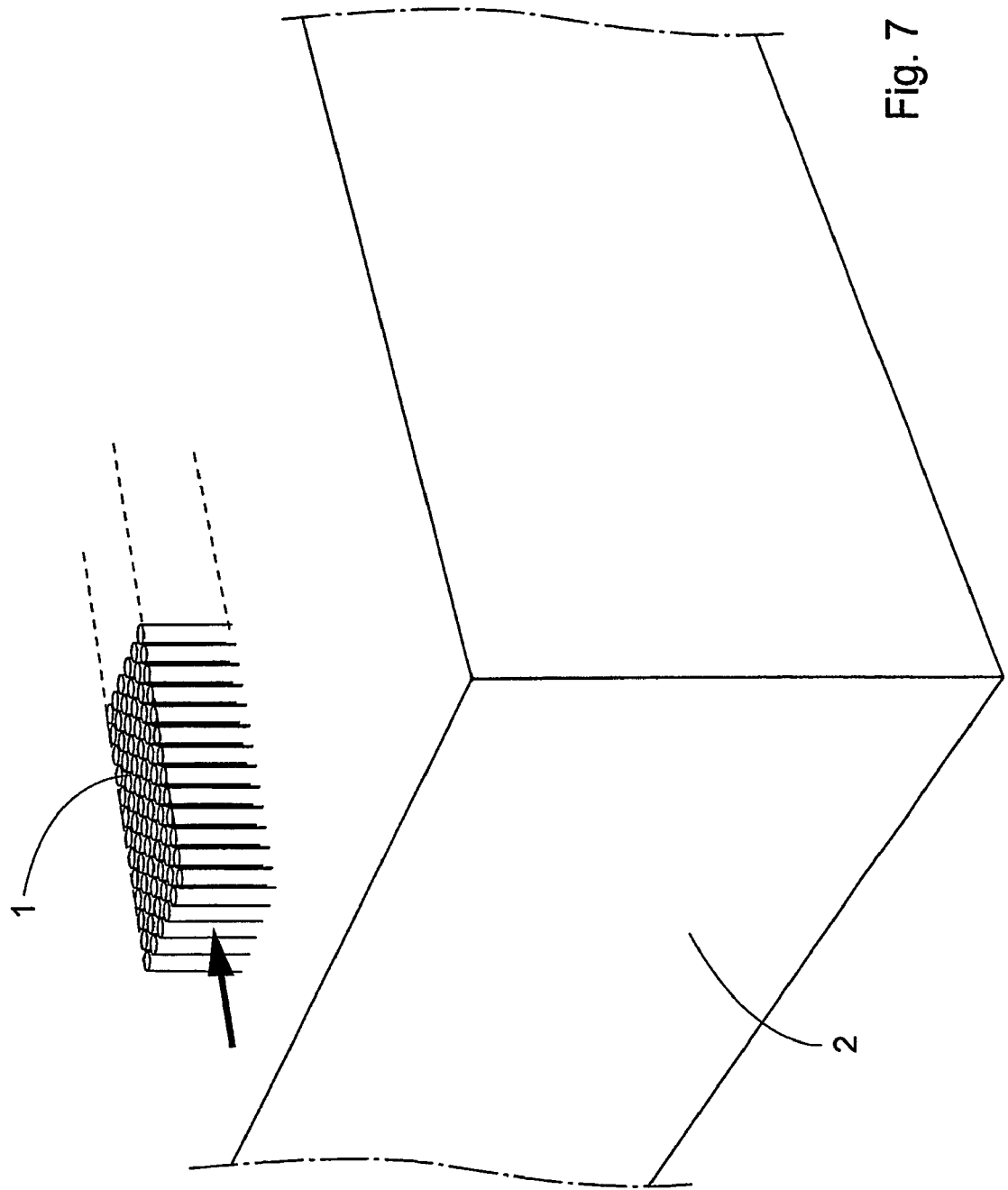
FIG. 7 shows a perspective view of one embodiment of a flow path where the capillary structure is formed of micro posts having a circular cross section; with no walls nor cover which would significantly contribute to the capillary action, according to the present invention.

FIG. 7 shows schematically a flow path consisting of a multitude of circular micro posts 1 on a surface 2. The micro posts can naturally have any cross section, height and ceter-to-center distance, as long as the parameters are chosen such that capillary flow is induced. The direction of the capillary flow is indicated by the black arrow. In FIG. 7, the support 2 is schematically indicated as having a thickness comparable to the height of the micro posts. While this is not ruled out, the most frequently encountered supports will be considerably thicker. FIG. 7 is thus only a schematic illustration.

A device according to the invention may comprise a support and at least one flow path consisting of micro structures as shown in FIG. 7. However, for most practical applications, a multitude of flow paths forming a channel system is required. The individual channels connect different functional regions, means or devices, such as reaction chambers, separation media etc.

When the properies of the columns and their properties, such as their material, their shape and/or distance, and optionally also the properties of the substrate, are selected properly with due consideration taken to the liquid to be transported, it will become possible to create a capillary flow through said structure, in the direction of the arrow if a liquid sample is place at the end where the arrow points, without any significant leakage out from the structure and onto the surrounding substrate surface.

Thus, the basic structure embodying the inventive concept is a substrate having at least one flow path provided in or on its surface. This flow path or channel is formed by column like micro structures or micro posts, protruding from surface of said support. The characteristic feature of the flow path and the micro posts therein is that the dimensions of said posts and the distance between said posts are selected such that capillary flow of liquids can be maintained therein. In particular, the distance between said columns is in the range of 0.1-1000 μm, preferably 1-100 μm. The columns are preferably higher than 1 μm, more preferably higher than 10 μm. Most preferably said micro posts have a high aspect ratio, that is a width to height ratio greater than 1:2.

Figure 14:
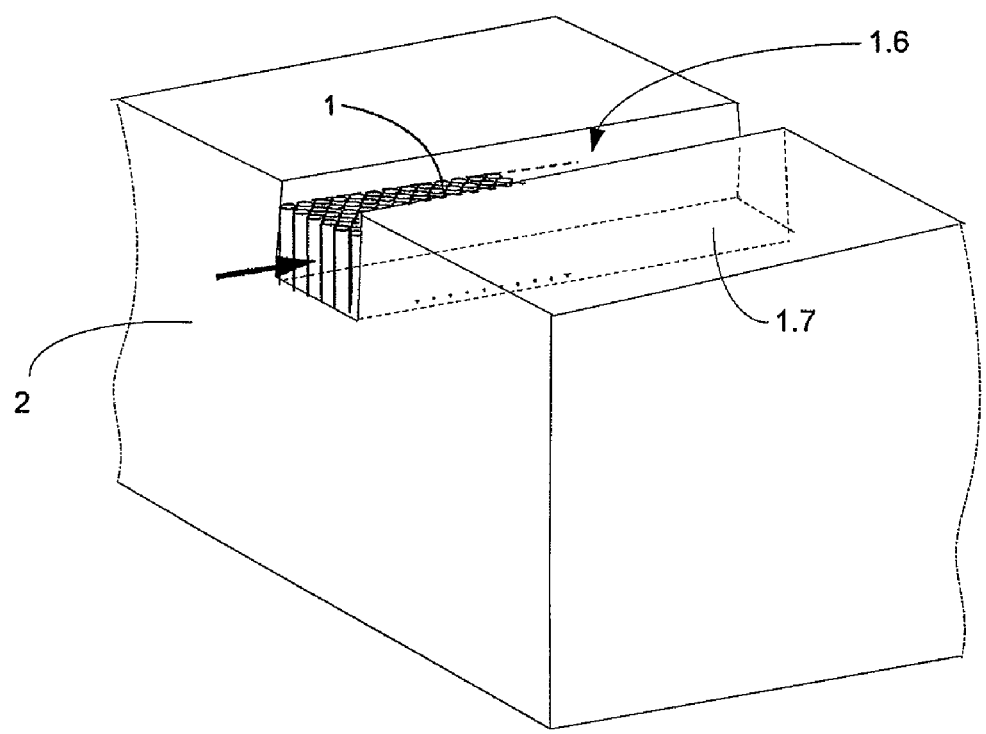
FIG. 14 shows a perspective view of one embodiment of a flow path where the capillary structure is formed of micro posts in a groove of a substrate, according to embodiments of the present invention.

It is understood that the micro posts can be either positioned within a secondary structure on the surface, with reference to FIG. 14, such as a groove (1.6) or a depressed area, or directly on the surface, protruding there from. When the micro posts are in a secondary structure, such as a groove in a substrate (2), the flow path will have a bottom (1.7) located beneath the general substrate surface, and more or less vertical side walls, together with the bottom forming a channel. The capillary action inducing and/or maintaining the flow is however caused essentially by the interaction between the liquid and the micro posts.

However, according to a preferred embodiment, the micro posts or columns are laid out as regions, preferably elongated, of upstanding columns, without any delimiting side walls. All functions and features that have been or will be discussed herein with reference to ordinary channels, are equally applicable to this type of structure, which thus is fully within the scope of the inventive concept as defined in the claims.

Figure 8:
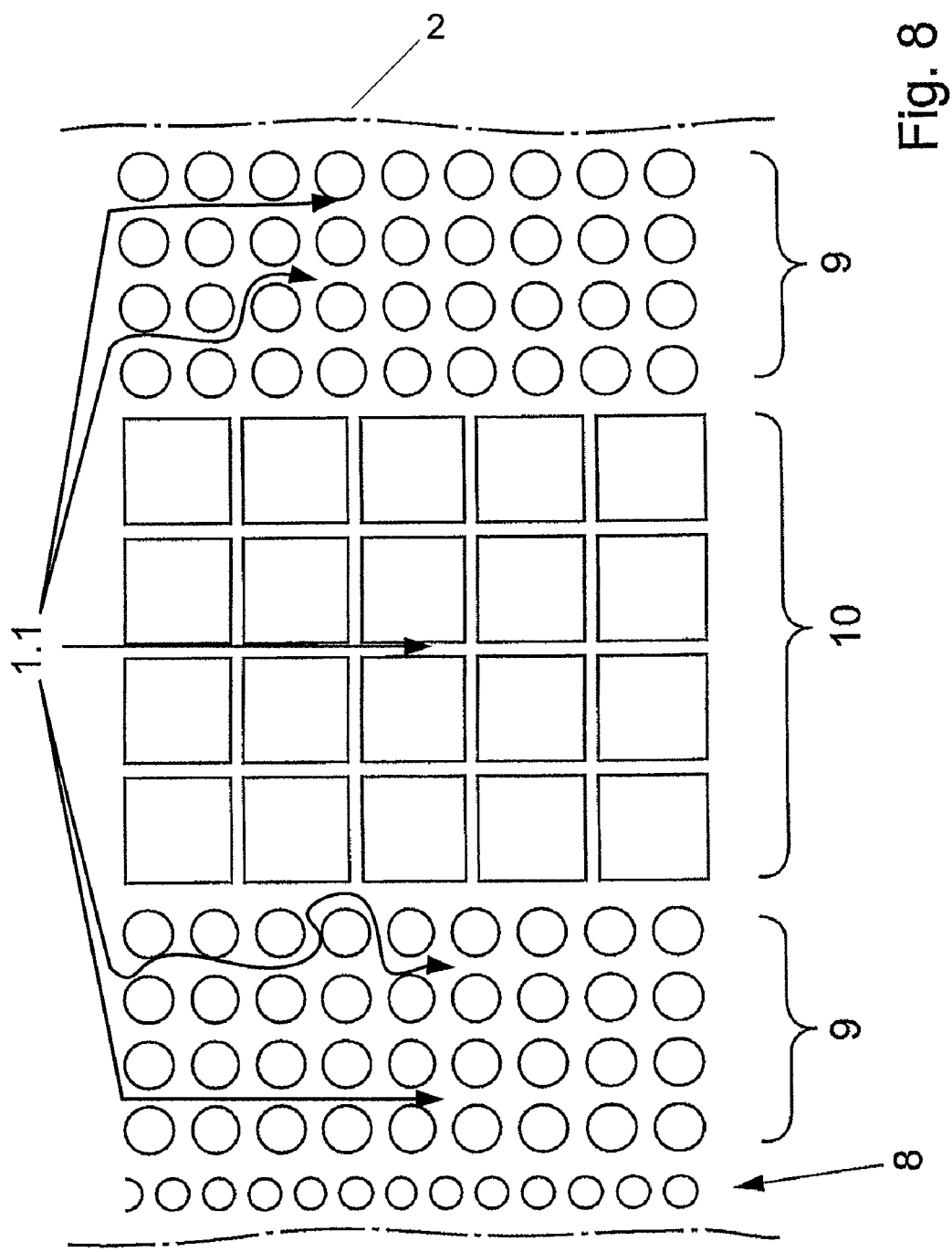
FIG. 8 illustrates one embodiment of a flow path (1.1) according to the present invention comprising zones with capillary structures or micro posts having different cross sections and different dimensions in adjacent zones.

According to a further embodiment of the present invention, the flow path is subdivided into zones wherein the columns can have different column height, diameter, geometry and/or different column density, i.e., number of micro-posts per unit area. FIG. 8 is a schematical illustration of this embodiment. A plurality of micro-posts 1 are provided in close proximity in adjacent groups are indicated 8, 9 and 10 and the differences shown as different size, shape and spacing only for the sake of illustration. Such groups can form an array, having desired functionality. Preferably said groups form a gradient, which can be continuous or discontinuous, preferably continuous.

In the embodiment shown in FIG. 8, a first more dense zone 8 is provided, where the micro structures have a smaller diameter and smaller distance. Such zone can act as a sieve or "fence" preventing larger particles, e.g. cells from passing. Next, there is a zone 9 with posts having relatively large spacing between them. This can serve to temporarily decrease the time for a liquid-solid face interaction in a desired region, e.g. if it is desired that the sample be exposed to some surface bound moiety for a specified time, in order for a particular reaction to proceed to a reasonable completion etc. After this low velocity region there is provided a zone 10 of larger micro posts (squares in the shown example) having fairly narrow passages between them. After this region, a second zone 9 similar to that is provided. Based on the information given in this description and the examples, a skilled person can design various combinations, according to the desired purpose.

Figure 9:
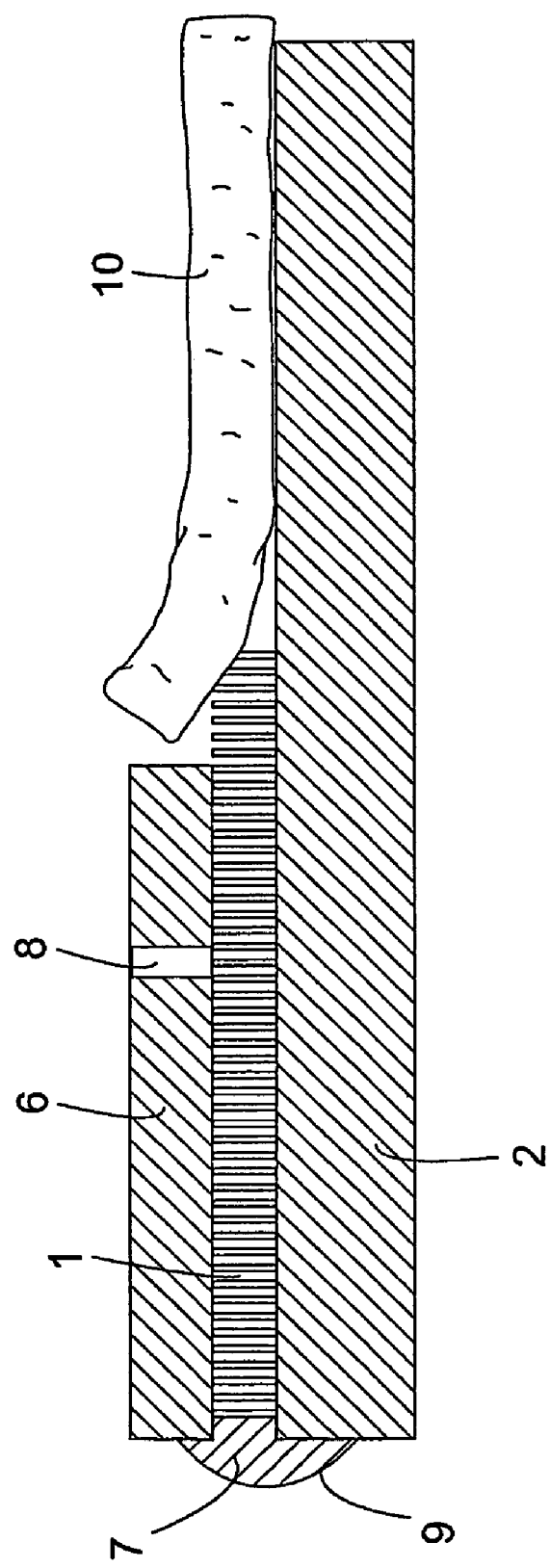
FIG. 9 shows schematically in cross section perpendicular to the plane of the device, the use of a bibulous material for maintaining or enhancing flow in a flow path according to the present invention.

According to another embodiment of the invention, the capillary flow path or paths has/have integrated surfaces or zones composed of bibulous material capable of capillary transport. This is schematically illustrated in FIG. 9 which shows a simple application of this concept.

In this case there is a closed channel structure comprising a plurality of micro-posts 1 filling the channel. The structure has a bottom substrate 2 and a cover 6, the substrate also forming side walls (not shown), and having an input aperture or hole 7, an optional further aperture or hole 8, and an exit aperture (not shown). If a drop 9 of liquid is applied to the input aperture 7, a capillary flow will immediately begin, and will continue to draw liquid from the drop until the flow reaches the exit, where no further capillary action will occur. However, if a bibulous material such as pad 10 of filter paper or the like of sufficient size, is applied at, within or in contact with the exit aperture, this material will by its capability of drawing liquid act as a "flow sink", i.e. it will absorb the liquid that exits from the channel, thereby enabling an essentially continuous flow through the channel.

Another embodiment having a flow sink, is that of the closed channel ending in an open region or zone of micro posts, said region having a relatively large area as compared to the channel. This large region will act as a flow sink in the same sense as the bibulous material discussed above. If e.g. heating means is provided to heat this region, evaporation of the liquid can be induced, thereby creating a sink that in principle could be maintained indefinitely. Evaporation of the liquid will also make possible the capture of components present in the flow, at a desired location and at a desired time in the device or process employing such device.

Figure 10:
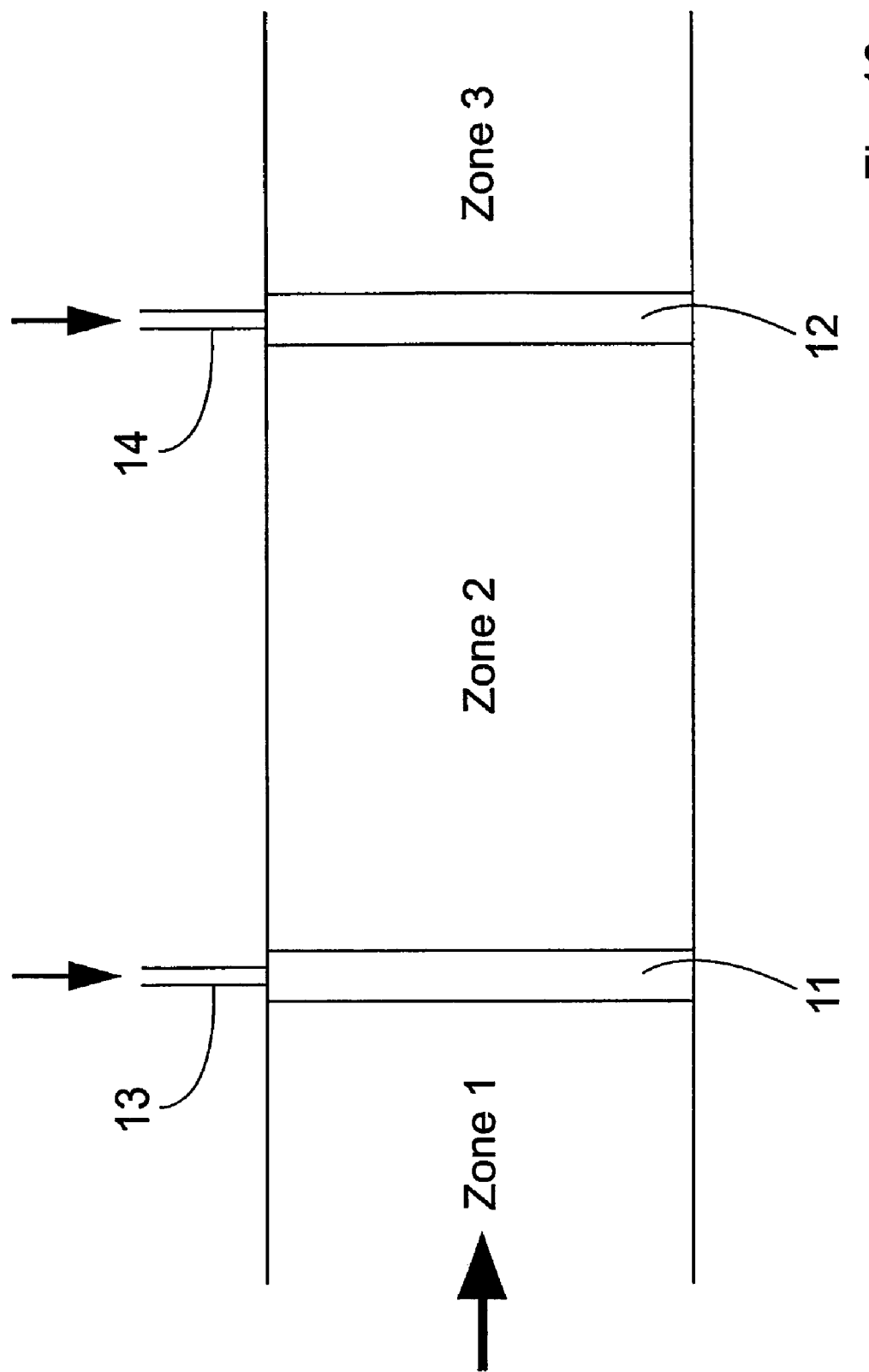
FIG. 10 shows schematically how a flow path according to the present invention can be divided into zones, separated by "bathers" preventing the capillary flow, and means for resuming or re-starting the flow.

FIG. 10 shows schematically another embodiment and application of the flow path structures according to the invention, the flow path comprising a plurality of consecutive micro fluidic structures, interrupted by zones without such structures, i.e. a small space or discontinuity 11 and 12, said discontinuity acting as capillary barriers, preventing liquid from being transported across the zones without assistance. The direction of the liquid flow is illustrated with the large horizontal arrow.

The discontinuities can be bridged or assisted transport can be brought about e.g. by applying a pressure pulse, whereby the capillary barriers provided by the voids are broken. The means for creating the pulse can be implemented by providing a very small channel 13 and 14 opening into the spacing, and for example momentarily applying sub-pressure (indicated with vertical arrows) in said channels. At the other end of the channel some means for providing a slight sub-pressure can be provided, whereby liquid from the regions on each side of the discontinuity will be forced into it, and when the gap is filled, capillary flow will again be resumed. This requires a closed system. In an open system (and in a closed), the small channel can be used to introduce liquid to fill the gap, thereby restoring a flow connection so as to resume the capillary flow.

Figure 11:
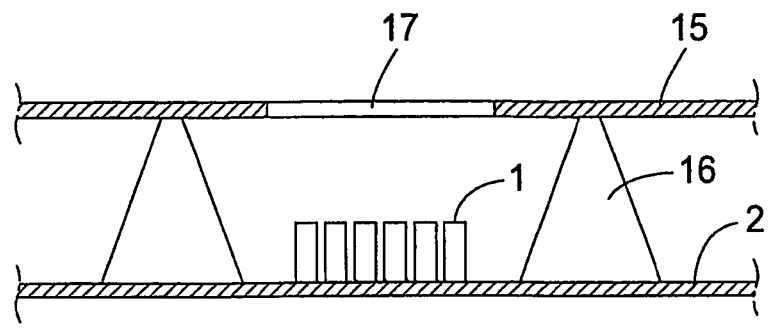
FIG. 11 shows schematically a cross section of a device having micro structures forming a flow path on a surface, and a separate lid, not significantly contributing to the capillary flow.

FIG. 11 shows a schematic partial view of a device according to the invention, where micro posts 1 are provided on a substrate 2, said substrate having larger protrusions 16 for carrying a cover or lid 15, said protrusions defining a distance between the surface the substrate and the lid considerably larger that the height of the micro posts, and such that no capillary interaction between the substrate and the lid can arise. The same applies to an alternative embodiment where the micro posts are located in grooves or depressions in the surface. The cover or lid 15 may further have apertures or holes 17, said holes preferably indication points for adding a sample or a reagent, for reading a result or for following the advancement of the reaction/reactions taking place on the substrate.

According to a preferred embodiment, the cover or lid is attached to the protrusions 16 only after the surface of the substrate has been functionalized or customized, i.e. after the addition of the necessary reagents and/or functionalities.

Figure 12:
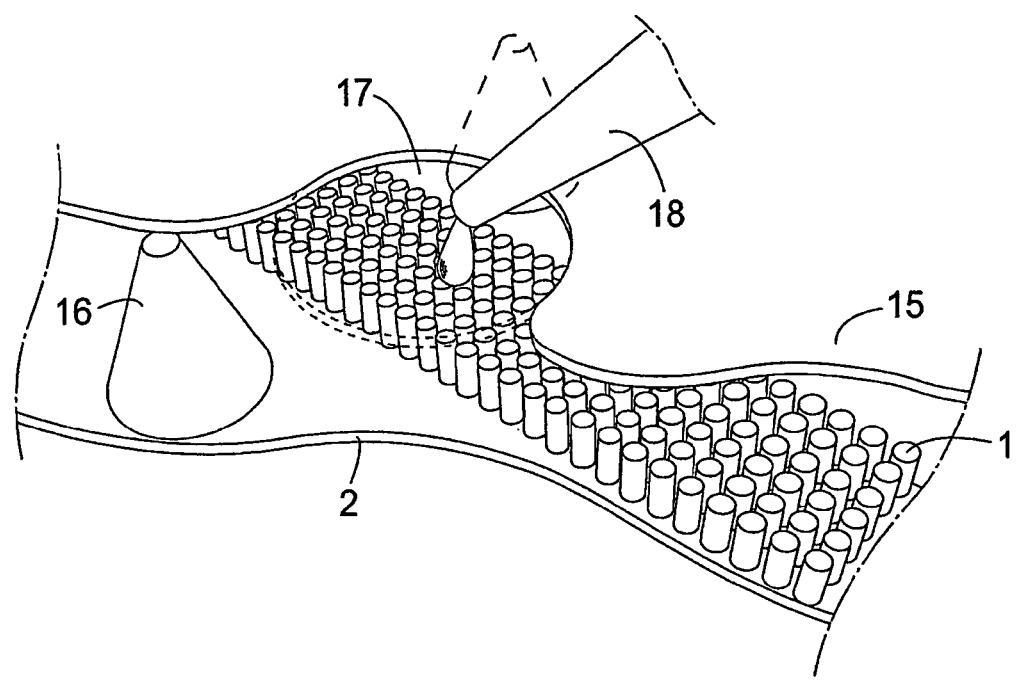
FIG. 12 shows schematically a partial exploded view of a device according to the invention, and as illustrated in FIG. 11, where a drop of liquid, e.g. a sample, is being added with a pipette through a hole in said separate lid.

FIG. 12 shows schematically an exploded view of the embodiment of FIG. 11, where a pipette tip 18 is shown deposition of a drop of a liquid through an opening 17 on a flow path according to the invention.

Figure 13:
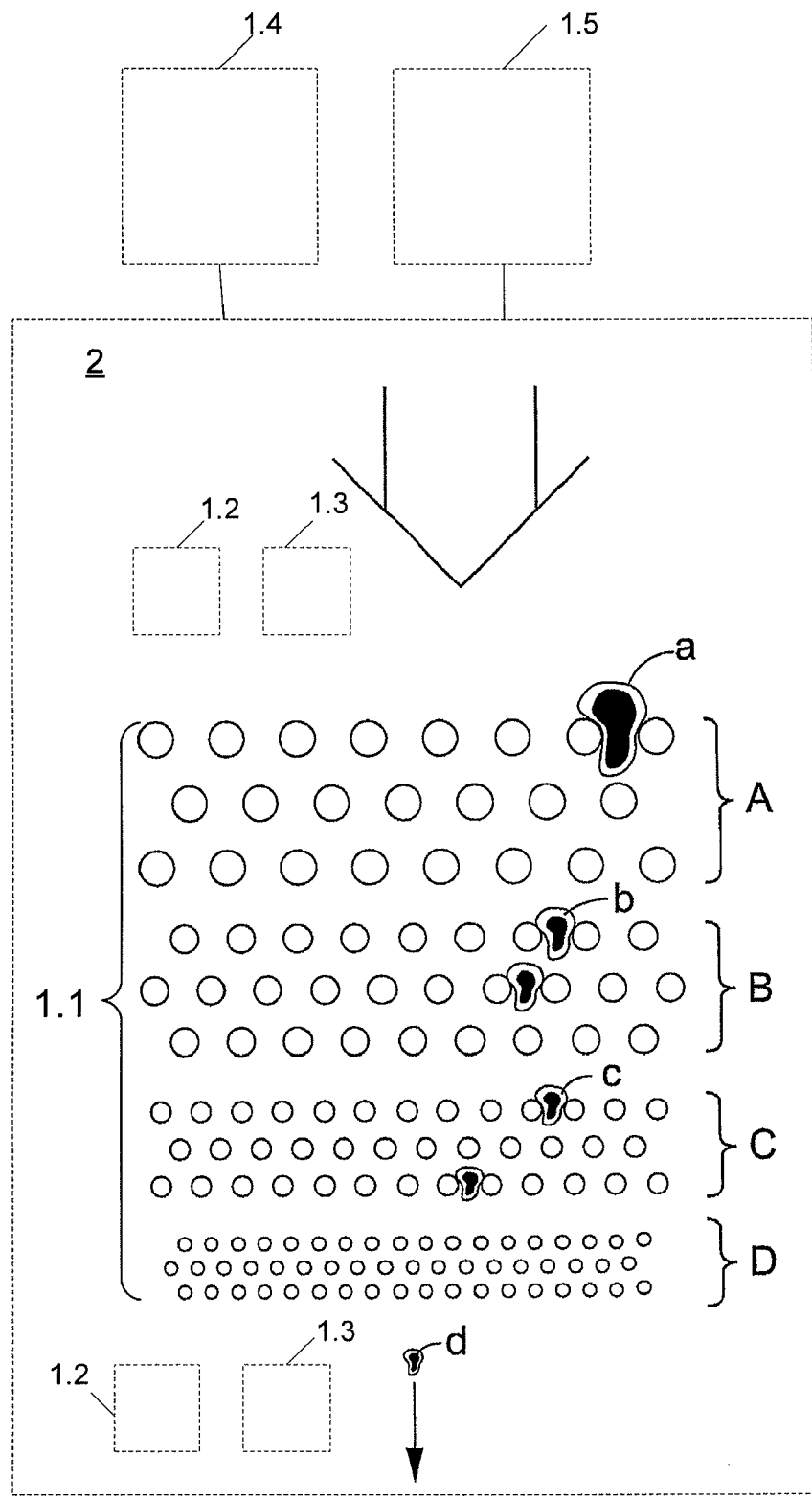
FIG. 13 shows schematically an embodiment where micro post of different size and/or functionality form a discontinuous gradient.

FIG. 13 illustrates an embodiment where groups of micro structures within a continuous flow path (1.1) form a gradient with respect to at least one property, e.g. the shape, size, center-to-center distance or a functional/chemical property. In the figure, the flow path comprises a discontinues gradient with respect to the size and center-to-center distance of the micro structures, represented by the groups A, B, C and D. A gradient like this can function to delay the passage of biological or chemical entities, such as particles, cells, organelles, macro molecules or the like, in a desired manner, or separate such entities. Entities captured in zone A are illustrated by the shape "a", entities captured in zone B with "b" and so on. The shape "e" illustrates entities that pass unhindered through the gradient.

In further embodiments, the flow paths can comprise integrated surfaces or zones containing a number of different functional elements or devices for performing a number of different operations on the media located within or in association to the flow paths. Examples of such functional elements or devices are electrodes (1.2) and/or other means of electrical manipulation of liquids and reagents. The electrical manipulation can e.g. comprises oxidation/reduction of species. Other representative examples of functional devices are optics and other means to manipulate light e.g. for the purpose of measuring concentrations by absorbance, inducing conformational changes by light irradiation.

Magnets or means for detection of magnetic substances (1.3) can also be arranged in or around the flow paths. Thereby, magnetic particles can be trapped and retained at desired locations in the structure, and the magnetic property of the particles can thereby be used as a marker or indicator of successful transport to a certain point in the system. Furthermore, magnetic particles can be coated with substances with biological affinity and used in different kinds of assays.

Furthermore, means for the manipulating of temperature with means for heating and/or cooling (1.4) can be provided in selected locations in a flow path according to the invention. Thereby a number of interesting functions can be performed such as, chemical reactions, incubation, thermal curing, PCR reactions, evaporations, drying etc.

Moreover, means for applying energy (1.5) may apply energy to one or more selected segments so as to induce a forced transport across the flow stop. The means for applying energy may be a pressure pulse generator, an ultrasound generator, or an electromagnetic radiation means, for example.

Within the flow path structures according to the invention there can be provided particles within or in association to the flow paths, at least in one of the zones containing micro structures such as micro posts or columns, where there is subdivision between zones with and without these structures. The particles can thereby be bound by physical forces to said substrate, or chemically bound, e.g. covalently bound to said substrate. Alternatively, said particles can be mechanically trapped within the zone (zones) containing said structures.

According to a preferred embodiment, the substrate has reactive substances attached to its surface. Such reactive substances are used in connection with detection of substances of chemical or biological origin. The reactive substances are used in connection with immobilisation of substances of biological as well as non-biological origin, i.e. they are provided as sites to which the substances to be immobilized can react so as to become bound to the substrate.

Another application of a reactive substance provided on the substrate is the use thereof in connection with separation of substances of biological as well as non-biological origin, where the substance can be selectively reactive with a species that one wishes to separate from another in a mixture.

The surfaces of a channel in a structure according to the invention can be modified by chemical or physical means. Such a modified surface can thereby be used in connection with detection of substances of biological and chemical origin. A modified surface of this kind can be used in connection with immobilisation of substances of biological as well as non-biological origin. It can also be used in connection with separation of substances of biological as well as non-biological origin.

Still another application of the flow path or channel structure according to the invention, is that the flow paths are used as means for multi spot detection, whereby said paths optionally have particles provided therein, said particles having chemically reactive groups or substances with bio-affinity bound in the micro spot area.

Other suitable applications of flow path structures according to the invention is the measurements of the amount of an analyte in a biological sample, e.g. in blood, serum, plasma, urine, cerebral spinal fluid, tears, amniotic fluid, semen or saliva, the measurements preferably being based on specific biological interactions.

A specific application is that said analyte is measured by immunological means.

The analyte can also be detected by specific interactions using poly- or oligonucleotides, preferably single stranded nucleic acids or aptameres.

The flow path structures according to the invention can also be used for the separation of cells, and for the screening of synthetic or biological libraries.

As discussed above, the notion of a "channel" for the purposes of the present invention goes beyond the ordinary concept of a channel, by allowing entirely open structures having no physical delimitations except for a bottom substrate on which the micro post or column structures are provided.

However, when the channel or flow path comprises a groove (i.e. having a bottom and side walls), there are two options: i) to leave the channel open upwards, and to place a top cover so as to make a closed system.

These two different embodiments have certain merits for different applications. In cases where it is desirable to manipulate the liquid that is transported and/or the substances transported by said liquid, it may sometimes be more convenient to have unrestricted access from above, such as for the purpose of adding reagents at desired points in the structure, to apply direct heat, or to perform other manipulations at more or less arbitrarily points.

Certain systems may be very sensitive to oxygen, and therefore it may be absolutely necessary to exclude the sample liquid from atmospheric exposure. If the micro-fluidic structure is covered, there can be provided access openings in said cover for enabling introduction of e.g. reagents, gas, liquids, or samples into said structure. Such access openings can also be used for connecting external equipment, e.g. via suitable tubing or the like.

However, both these embodiments are within the inventive concept.

Manufacturing of such microstructures could in its simplest form be done by direct curing of a photosensitive mono- or pre-polymer deposited on a substrate, employing a mask through which light is irradiated to initiate curing, and thereafter rinsing away the un-cured areas (thick film photo-resist process).

An other straightforward method is through replication of an original into a polymer. The original could be manufactured in silicon through a DRIB-process (Deap Reactive Ion Etch) where high aspect ration structures could be produced. Other ways of producing such originals could for instance be through laser processing, electro discharge methods, Free Form Manufacturing (FFM), electrochemical or chemical etching, gas phase etching, mechanical processing, thick film photoresist processes or combinations thereof, of or on a substrate of, for instance, silicon, glass, quartz, ceramic, metal or plastic material. e.g. PMMA or Teflon.

The most straight forward method of replication would be casting of a mono- or pre-polymer over an original with the desired negative shape. Other ways of producing the polymer replicas could involve injection molding or embossing of thermoplastics or thermoset materials.

If the original in some aspects are not withstanding the replication process a an intermediate replica in a suitable material (a stamper) could first be produced from the original. Examples of such stamper process could be to first deposit a conducting layer on top of the original and thereafter through electroplating form a negative from the original. Certain plating materials such as Nickel lend themselves also to the repeated and non-destructive production of copies of the stamper. This gives the possibility to both change polarity from negative to positive as well as producing series of identical stampers for large volume production of replicas. Other examples of stamper manufacturing could be in a well chosen polymer given the negative shape of the original in a casting, embossing or injection molding process. The same possibility of repeatedly and non-destructively making copies of the stamper could also be true for polymer stampers.

As mentioned above the micro-fluidic structure of the invention may, of course, be designed for a plurality of micro-fluidic purposes. Among those are e.g. capillary chromatography, ion-exchange chromatography, hydrophobic interaction chromatography, immunoassays, hybridization assays and other molecular biology assays, micro reaction cavity procedures, miniaturized liquid communication units, biosensor flow cells, etc. Reaction cavities constructed in accordance with the invention may, for example, be used for various forms of solid phase synthesis, such as peptide or oligonucleotide synthesis. PCR, DNA solid phase sequencing reactions, sample treatment and detection, just to mention a few.

The micro fluidic structures according to the invention can be made in different ways. One convenient method is outlined above, but it is also possible to make the structures from separate parts which are assembled after column formation has taken place in a suitable substrate.

In the following, the invention will be illustrated by specific non-limiting examples.

EXAMPLES

Example 1

Flow in Open Channels with Columns Made of Silicon

Flow channels were produced by etching silicon wafers by a standard method well known to a person skilled in the art. The resulting silicon chips had a length of 25 mm and a width of 5 mm. The area covered by columns was 10 mm long and 4 mm wide. The columns had a height of 100 μm and a diameter of 20 μm, the center-to-center distance being 30 μm.

Capillary flow was tested with purified water, buffer and blood plasma. A wicking membrane (Whatman WF 1.5) was placed a few mm in at the distal end of the chip to facilitate the liquid flow.

8 μl of water added to the structure took between 60 and 90 seconds to flow across the structure provided with columns. A similar flow speed was measured with a buffer containing 50 mmole/l sodium phosphate, 6% bovine serum albumin, 0,2% Tween 20, pH 7.5. Blood plasma was slightly faster than water and buffer.

Example 2

Flow in Open Channels with Columns Made of Epoxy Plastic

Flow channels were produced by first etching silicon wafers by a standard method well known to a person skilled in the art. A thin layer of epoxy was the applied uniformly to the silicon wafer. The resulting epoxy covered chips had a length of 25 mm and a width of 5 mm. The area covered by columns was 10 mm long and 4 mm wide. The columns had a height of approximately 90 μm and a diameter of approximately 20 μm, the center-to-center distance being close to 30 μm.

Capillary flow was tested with purified water and buffer. A wicking membrane (Whatman WF 1.5) was placed a few mm in at the distal end of the chip to facilitate the liquid flow. The chip was pretreated (one hour, room temperature) with a buffer containing 50 mmole/l sodium phosphate, 6% bovine serum albumin, 0.2% Tween 20, pH 7.5 prior to addition of water or buffer. 8 μl of water added to zone 1 took about 90 seconds to flow through the zone with columns. Similar flow speed was found with a buffer containing 50 mmole/l sodium phosphate, 6% bovine serum albumin, 0,2% Tween 20, pH 7.5.

The above examples demonstrate that it is possible to create open flow paths consisting of micro structures and that these function, i.e. that the necessary capillary forces are created and that liquid transport takes place.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

The invention claimed is:

1. An open micro fluidic system comprising:
   a substrate having a non-porous surface;
   a first plurality of microposts protruding from said non-porous surface of said substrate and defining at least one flow path in which liquid samples can be treated by desired procedures, wherein said at least one flow path is laid out for transport of liquid samples, wherein the at least one flow path extends in a lateral direction which is transverse to the protruding microposts; wherein cross sections of said microposts and the center to center spacing between each of the first plurality of microposts spontaneously induces a passive capillary action in a liquid sample applied to said at least one flow path, so as to force said liquid to move laterally away from where said liquid sample was applied, said first plurality of microposts further including at least one biological binder having an affinity to at least one component of a liquid sample introduced along said at least one flow path;

a sample receiving area disposed prior to said at least one flow path and fluidly connected therewith; and a sample collecting sink disposed after said at least one flow path on said substrate and fluidly connected with said at least one flow path, said sample collecting sink having an area which is larger than the area of the at least one flow path extending from said sample receiving area, said sink having a second plurality of microposts protruding from said substrate surface, said second plurality of microposts having cross sections and center to center spacing between each of said microposts that further induce capillary flow from said flow path to said sample collecting sink and wherein of the cross sections and center to center spacing of said second plurality of microposts are different those than of said first plurality of microposts.

2. The micro fluidic system according to claim 1, wherein said substrate is provided with grooves having a bottom surface and side walls, said first plurality of microposts protruding from the bottom surface of said grooves and wherein the passive capillary action is caused essentially between said liquid and the microposts.

3. The micro fluidic system according to claim 2, wherein each plurality of microposts has a height dimension, wherein said at least one flow path is covered by a lid, and wherein said lid is positioned at a distance from the surface of the substrate to the lid that is considerably larger than the height dimension of each plurality of microposts so that no capillary action between the substrate and the lid can arise.

4. The micro fluidic system according to claim 3, wherein the lid has access openings for enabling introduction of at least one of reagents, gas, liquids, and samples into said at least one flow path.

5. The micro fluidic system according to claim 1, wherein the substrate is essentially flat and each plurality of microposts protrude from said substrate.

6. The micro fluidic system of claim 1, wherein the first plurality of microposts are grouped in adjacent segments so as to provide a capillary barrier discontinuity between such segments, the capillary barrier discontinuity having a finite distance, preventing the capillary flow between said segments, thereby providing a flow stop.

7. The micro fluidic system according to claim 6, further comprising means for applying energy to one or more selected segments to induce a forced transport across the flow stop.

8. The micro fluidic system according to claim 7, wherein said means for applying energy is selected from a pressure pulse generator, an ultrasound generator, and an electromagnetic radiation means.

9. The micro fluidic system according to claim 6, further comprising means for applying liquid to said discontinuity to provide a bridge across said discontinuity so as to induce a flow there across.

10. The micro fluidic system according to claim 1, wherein surfaces of the microposts in said at least one flow path have at least one of a chemical, biologic or physical functionality.

11. The micro fluidic system according to claim 10, wherein the first plurality of microposts have chemically reactive groups on their surface.

12. The micro fluidic system according to claim 10, wherein the first plurality of microposts have hydrophilic groups on their surfaces.

13. The micro fluidic system according to claim 10, wherein the first plurality of microposts have positively and/or negatively charged groups on their surfaces.

14. The micro fluidic system according to claim 11, wherein the first plurality of microposts have hydrophobic structures on their surfaces.

15. The micro fluidic system according to claim 10, wherein said at least one functionality is applied to the first plurality of microposts in the entire at least one flow path or limited to a portion thereof.

16. The micro fluidic system according to claim 11, wherein said first plurality of microposts have a property that is selected from the group consisting of a diameter of 20 µm, a height of 100 µm, a square shape, a circular cross section, a hydrophobic surface coating, a hydrophilic surface coating, and a micropost spacing distance from center-to center of 30 µm.

17. The micro fluidic system of claim 1, wherein particles are provided within said at least one flow path.

18. The micro fluidic system according to claim 17, wherein said particles are chemically or physically bound to the substrate, or mechanically trapped within a region comprising at least a portion of said first plurality of microposts.

19. The micro fluidic system of claim 1, wherein said at least one flow path has integrated zones or delimited surfaces containing electrodes or other means for electrical manipulation of liquids and/or reagents.

20. The micro fluidic system according to claim 1, wherein said at least one flow path has integrated zones or delimited surfaces containing optical elements or other means for transmitting, focusing, reflecting or absorbing light.

21. The micro fluidic system according to claim 1, wherein said at least one flow path has integrated zones or delimited surfaces containing means for the regulation of the temperature in said zone.

22. The structure according to claim 1, wherein said first plurality of micro posts are defined by an aspect ratio of at least 1:2.

23. The structure according to claim 1, wherein said first plurality of micro posts are defined by an aspect ratio of at least 1:5.

24. The structure according to claim 1, wherein said first plurality of micro posts are defined by a diameter of approximately 20 micrometers, a height of approximately 100 micrometers and a center to center distance between adjacent micro posts of approximately 30 micrometers.

* * * * *